United States Patent [19]
Marshall

[11] Patent Number: 5,888,500
[45] Date of Patent: Mar. 30, 1999

[54] BIOLOGICAL CONTROL AGENT BIOCARRIERS AND METHOD OF FORMATION

[76] Inventor: Lucia G. I. Marshall, 5781 Summit Meadow Dr., St. Charles, Mo. 63304

[21] Appl. No.: 721,609

[22] Filed: Sep. 26, 1996

[51] Int. Cl.$^6$ .................................................. A01N 63/00
[52] U.S. Cl. ........................ 424/93.1; 424/405; 424/408; 424/409; 514/783
[58] Field of Search ........................... 424/405, 44, 93.1, 424/400, 408, 409, 489; 514/783

[56] References Cited

U.S. PATENT DOCUMENTS

| | | | |
|---|---|---|---|
| 3,885,052 | 5/1975 | Starr | 426/250 |
| 4,036,228 | 7/1977 | Theeuwes | 128/260 |
| 4,560,527 | 12/1985 | Harke et al. | 264/500 |
| 4,716,039 | 12/1987 | Rogoff et al. | 424/93 |
| 5,019,564 | 5/1991 | Lowe et al. | 514/75 |
| 5,023,080 | 6/1991 | Gupta | 424/405 |
| 5,055,300 | 10/1991 | Gupta | 424/409 |
| 5,079,005 | 1/1992 | Gupta | 424/408 |
| 5,210,184 | 5/1993 | Chajuss | 530/370 |
| 5,439,911 | 8/1995 | Ohtsuka et al. | 514/256 |

FOREIGN PATENT DOCUMENTS

| | | |
|---|---|---|
| 1642233 | 4/1971 | Germany . |
| 32 42 798 A1 | 11/1982 | Germany . |
| 195 09 936 C | 3/1995 | Germany . |
| 2 242 130 | 9/1991 | United Kingdom . |
| PCT/US91/01744 | 3/1991 | WIPO . |
| WO 95 311101 | 11/1995 | WIPO . |
| WO 95/31101 | 11/1995 | WIPO . |

OTHER PUBLICATIONS

AN 93–185350 XP002052620 abstract., May, 1993.
Database WPI Section Ch, Week 9323 Derwent Publications Ltd., London, GB; Class B07, AN 93–185350 XP002052620 & JP 05 112 772 A (Sanei Toka KK), 7 May 1993, abstract.
Patent Abstracts of Japan, vol. 11, No. 176 (C–426), 5 Jun. 1987 & JP 62 004209 A ( Takeda Chem Ind), 10 Jan. 1987, abstract.

*Primary Examiner*—James Ketter
*Assistant Examiner*—Iren Yucel
*Attorney, Agent, or Firm*—Grace J. Fishel

[57] ABSTRACT

A biocarrier loaded with up to 60% by weight of a mixture including a biological control agent. The biocarrier is derived from the residual cell mass remaining after lipids and soluble proteins and sugars have at least in part been removed from crushed or ground oil seeds. The biological control agent is an agrochemical, biopesticide or mixtures thereof. When the product is formulated as a granule, tablet or briquette it has good hardness and produces substantially no dust, thereby reducing operator exposure to the biological control agent.

23 Claims, No Drawings

5,888,500

BIOLOGICAL CONTROL AGENT BIOCARRIERS AND METHOD OF FORMATION

BACKGROUND OF THE INVENTION

1. Field of the Invention

The present invention relates to a biological control agent biocarrier derived from the residual cell mass remaining after lipids and soluble proteins and sugars have at least in part been removed from crushed or ground oil seeds. The biocarrier can be loaded with up to 60% by weight of a mixture including a biological control agent and formed into a compactible powder that, for example, can be processed into granules, pellets, tablets or briquettes that do not crumble easily, thereby reducing operator exposure to dust carrying the biological control agent.

2. Brief Description of the Prior Art

The search for better, more economical and more ecologically sound carriers for biological control agents is a continuing one. The organic and inorganic carriers presently available are costly, have low absorbability, are nonbiodegradable or toxic, are not compactible, or have some combination of faults. For example, silica and clay are added to biocarriers derived from wood pulp to make them compactible. These biocarriers are objectionable because silica causes silicosis and is a known carcinogen.

SUMMARY OF THE INVENTION

The biocarriers useful in the present invention are a by-product of oil seed processing. When oil seeds such as soybeans, corn, oats, sesame, peanuts, etc. are crushed or ground and subjected to physical and chemical extraction processes to separate the edible from the inedible or undesirable parts not ordinary used for food, there remains a by-product waste stream having little or no economic value. This by-product comprises a residual cell mass including cell walls, membranes and microfilaments, which in the case of soybeans is primarily the carbohydrate portion of the soybean cotyledon.

The above-mentioned by-product when provided in the form of discrete particles can be compacted into granules, tablets, briquettes, etc. which have good hardness so that when they are loaded with a mixture including a biological control agent, they do not dust, thereby reducing operator exposure to the biological control agent. The by-product has excellent absorptivity and can be loaded with up to 60% by weight of a mixture including a biological control agent. The biological control agent biocarriers can be formulated into a variety of forms including broadcast granules or into effervescing tablets when a gas producing distintegrant is added to the mix.

The benefits resulting from the use of the above-described biological control agent biocarriers include the basic environmental friendliness of the product, the versatility of the product in its variety of uses, the addition of value to crop waste, the recycling of nutrients back into the soil when the biological control agent biocarrier is applied and more desirable registration properties for EPA consideration.

Accordingly, it is an object of the invention to provide a novel biological control agent biocarrier for use in agriculture. It is another object of the invention to provide biological control agent biocarriers that reduce transport losses of ingredients into the environment. A further object is to make biocarrier formulations, e.g., water dispersible granules, as blanks for end-use formulators to which a biological control agent can be added in accordance with the present invention. Other objects and features of the invention will be in part apparent and in part pointed out hereinafter.

In accordance with the invention, a process for preparing a biological control agent biocarrier comprises the steps of (a) providing a biocarrier comprising a plurality of discrete particles which are the residual cell mass remaining after lipids, proteins and sugars have at least in part been removed from crushed or ground oil seeds, (b) mixing a biological control agent with the particles and (c) processing the resulting mixture into powder, flakes, granules, pellets, tablets or briquettes.

Another aspect of the invention concerns a delivery vehicle for delivering a biological control agent. The vehicle comprises a plurality of discrete particles derived from a residual cell mass remaining after lipids, proteins and sugars have at least in part been removed from crushed or ground oil seeds. The residual cell mass includes cell walls, membranes and microfilaments, loaded with up to 60% by weight of a mixture including a biological control agent.

The invention summarized above comprises the products and processes hereinafter described, the scope of the invention being indicated by the subjoined claims.

DETAILED DESCRIPTION OF THE INVENTION

The biocarriers used in the present invention are derived from oilseeds. In brief outline, the oil seeds forming the starting material are ground or crushed, the oil is extracted and then the soluble proteins and sugars are dissolved out into solution. The residual cell mass, which in the case of soybeans is primarily the carbohydrate portion of the soybean cotyledon, consists of cell walls, membranes and microfilaments and is separated from the solution and dried.

In the case of soybeans, for example, the soybeans are crushed or ground in conventional fashion, and passed through a conventional oil expeller. The oil is preferably removed by solvent extraction, using solvents normally employed for this purpose. The resulting solids, commonly referred to as high DPI soybean flakes, contain many ingredients including complex proteins, sugars, fibers and others. The proteins and sugars are dissolved out of the solids. This may be done by adding the flakes to an aqueous bath and adding a food grade alkaline material to raise the pH substantially above 7. Typical of such alkaline reagents is sodium hydroxide, potassium hydroxide, calcium hydroxide or other commonly accepted food grade alkaline reagents. The material is then extracted for a period of time sufficient to put the proteins and sugars in solution, usually about 30 minutes or so. The resulting liquor solution is separated from the solids, as by passing the material through a screen and/or centrifuging. The solids, the residual cell mass, is dried and then milled to a suitable size, e.g. between about 20 to about 200 microns, using a hammer mill followed by air-milling to obtain a suitable particle size distribution for used as described below.

A commercially available source of soybean residual cell mass is sold by Protein Technologies International under the trademark POLY-SOY. The composition of POLY-SOY is given below:

| ASSAY | LEVEL (% by weight) |
|---|---|
| Moisture | 10.0 |
| Protein (As is) | 12.0 |
| Protein (Dry basis) | 13.3 |
| Fat | 1.0 |
| Ash | 4.0 |
| Carbohydrate | 73.0 |
| Calcium | 1.0 |
| Phosphorus | 0.5 |
| Magnesium | 0.2 |
| Potassium | 0.95 |
| Sodium | 0.2 |
| Iron | 110 ppm |
| Manganese | 21 ppm |
| Zinc | 24 ppm |
| Copper | 2 ppm |

Loading capacity of the biocarrier for a mixture including a biological control agent in accordance with the present invention is affected by particle size and must be determined. When the loading capacity of the biocarrier has been determined, active ingredient formulations with the biological control agents may be prepared and loaded onto the carrier in an agrochemically effective amount. Because the natural oils have been removed from the residual cell mass, the biocarrier has high absorptivity, particularly for oils, which can be used to load the mixture with the biological control agent on the biocarrier. It has been found that up to about 60% by weight of material can be loaded on the biocarrier, by known means, e.g. absorption of a liquid suspension, followed by air drying, etc.

The term "biological control agents" includes agrochemicals, biopesticides or mixtures thereof. Included within the term "agrochemicals" are herbicides, fungicides, bactericides, acaricides, insecticides, gametocides, nematocides, algicides, rodenticides, molluscides, insect baits, repellents, pheromones, insect growth regulators, fertilizers, micronutrients, soil conditioners, growth regulators and the like, or mixtures thereof. It should also be understood that the term "agrochemical" includes agricultural, horticultural, fruticultural and floricultural use. The term "biopesticides" includes fungi, viruses, bacteria, toxins and the like, as well as mixtures thereof, including mixtures of biopesticides with agrochemicals. The biocarrier contains micronutrients that may be useful to the soil during crop treatment and may provide micronutrients to nurture any biopesticide during storage and application.

The term "agrochemically effective amount" is that quantity of a biological control agent, which when applied to an agricultural site in a conventional manner causes the occurrence of one or more of the sought after biological effects. The quantity of the biological control agent applied in a given composition will depend on the biological control agent itself, on the type of agrochemical activity inherent in the biological control agent, and on the degree of such activity sought to be achieved. The selection of the proper quantity of biologically active agent to be applied, however, is within the expertise of one skilled in the art.

The biological control agent can be added to the biocarrier as described above, with or without wetting agents or humectants or additional absorptive agents such as silica or clay. Other biocarriers derived from other plant material may be added in an amount from 0 to 50 percent by weight of the combined weight of the biocarriers. For example the addition of wheat, corn or oat materials, particularly oat protein, may improve the wetability and coating properties of the biocarrier. Other possible additives include dispersants, surfactants, emulsifiers, gas producing disintegrants, glidants or slip agents and other adjuvants. Suitable gas producing disintegrants include effervescing agents such as sodium or potassium bicarbonate with a food grade acid such as citric acid, etc.

The resultant biological control agent biocarriers may be formulated as dry flowables, water dispersible granules, broadcast granules, suspensions, emulsions, tablets, briquettes and so forth. When the product is formulated as a granule, tablet or briquette, it has good hardness and does not tend to crumble or dust, thereby reducing operator exposure to the biological control agent, a matter of considerable health concern. The product however can be readily dispersed in water for spray application or the like.

The following examples illustrate the invention.

EXAMPLE 1

Tablets were formed in a Colton Model 330, 2-ton press with the following biological carriers:

| Type | Particle size (mesh) |
|---|---|
| Ground corn cobs | <60 |
| Wood cellulose | <60 |
| Oat protein | <100 |
| Oat fiber | <100 |
| Oat hulls | <60 |
| Soy residual cell mass | <60 |

The tablets formed of soy residual cell mass, a biocarrier used in the present invention, compacted well and had good tablet strength. The tablets formed of with the other biocarriers failed to compact and/or formed tablets that were friable.

EXAMPLE 2

A biocarrier with a biopesticide having the following composition can be prepared as follows:

| Percent by weight | |
|---|---|
| 60 | Soy residue cell mass |
| 30 | Lagenidium |
| 5 | Sodium acid pyrophosphate |
| 5 | Sodium bicarbonate |

The biopesticide Lagenidium is blended into the biocarrier material and dried. The sodium acid pyrophosphate and sodium bicarbonate are then mixed in and the powder blend compacted in a tablet press. The tablets can be used to kill mosquito larvae.

EXAMPLE 3

A biocarrier with a herbicide having the following composition can be prepared from:

| Percent by weight | |
|---|---|
| 34 | Soy residue cell mass |
| 46 | Trifluralin |
| 7 | Citric acid |

-continued

| Percent by weight | |
|---|---|
| 7 | Sodium bicarbonate |
| 6 | Surfactant |

EXAMPLE 4

A broadcast biocarrier to which up to 60% by weight of a biological control agent can be added having the following composition can be prepared from:

| Percent by weight | |
|---|---|
| 70 | Soy residue cell mass |
| 30 | Oat protein |

Granules formed from the above mixture have excellent absorption properties for the biological control agent (e.g., 5% by weight pendamethalin) and excellent wetting and coating properties.

EXAMPLE 5

An effervescent biocarrier to which up to 60% by weight of a biological control agent can be added having the following composition can be prepared from:

| Percent by weight | |
|---|---|
| 70 | Soy residue cell mass |
| 20 | Oat protein |
| 5 | Citric acid |
| 5 | Sodium bicarbonate |

Granules formed from the above mixture have excellent absorption properties for the biological control agent (e.g., 25% by weight trifluralin) and dissolve easily in water.

EXAMPLE 6

A water dispersible granule for use in seed treatment can be prepared from:

| Percent by weight | |
|---|---|
| 40 | soy residue cell mass |
| 10 | Oat protein |
| 50 | Thiram (fungicide) |

In view of the above, it will be seen that the several objects of the invention are achieved and other advantageous results attained. As various changes could be made in the above methods and compositions without departing from the scope of the invention, it is intended that all matter contained in the above description shall be interpreted as illustrative and not in a limiting sense.

What is claimed:

1. A process for preparing a biocarrier for a biopesticide comprising the steps of:
   a) providing a biocarrier comprising a plurality of discrete particles obtained as a residual cell mass remaining after lipids and soluble proteins and sugars have at least in part been removed from crushed or ground oil seeds;
   b) mixing a biopesticide with said particles; and,
   c) processing the resulting mixture into powder, flakes, granules, pellets, tablets or briquettes.

2. The process of claim 1 wherein the particles of step a are obtained from soybeans and the biopesticide and an agrochemical are mixed with said particles.

3. The process of claim 2 wherein the agrochemical is a herbicide, fungicide, bactericide, acaricide, insecticide, gametocide, nematocide, algicide, rodenticides, molluscides, insect baits, repellents, pheromones, insect growth regulators, fertilizers, micronutrients, soil conditioners, growth regulators or a mixture thereof.

4. The process of claim 2 wherein the biopesticide is a fungus, virus, bacterium, toxin or a mixture thereof.

5. The process of claim 2 wherein a surfactant is added to said particles.

6. The process of claim 5 wherein a gas producing disintegrant is added to said particles.

7. The process of claim 1 wherein another carrier material obtained from a different plant is added to the biocarrier obtained from soybeans in an amount up to about 50 percent by weight based on the combined weight of the biocarriers.

8. A process for preparing a biocarrier for a biopesticide comprising the steps of:
   a) providing a biocarrier comprising a plurality of discrete particles obtained as a residual cell mass remaining after lipids and soluble proteins and sugars have at least in part been removed from crushed or ground soybeans;
   b) mixing a biopesticide, a surfactant and a gas producing disintegrant with said particles;
   c) forming granules, pellets, tablets or briquettes from the resulting mixture that do not crumble easily but disperse rapidly and form suspensions in a liquid carrier whereby little or no dust carrying the biopesticide comes off the granules, pellets, tablets or briquettes when the suspensions are formed, thereby reducing operator exposure to the biopesticide.

9. The process of claim 8 wherein the particles from step a are mixed with the biopesticide, the surfactant and the disintegrant and an agrochemical.

10. The process of claim 9 wherein the agrochemical is a herbicide, fungicide, bactericide, acaricide, insecticide, gametocide, nematocide, algicide, rodenticides, molluscides, insect baits, repellents, pheromones, insect growth regulators, fertilizers, micronutrients, soil conditioners, growth regulators or a mixture thereof.

11. The process of claim 9 wherein the biopesticide is a fungus, virus, bacterium, toxin or a mixture thereof.

12. A delivery vehicle for delivering a biopesticide comprising a plurality of discrete particles obtained as a residual cell mass remaining after lipids and soluble proteins and sugars have at least in part been removed from crushed or ground soybeans, said residual cell mass including cell walls, membranes and microfilaments and said residual cell mass loaded with up to 60% by weight of a mixture comprising a biopesticide.

13. The vehicle of claim 12 wherein the mixture further comprises an agrochemical.

14. The vehicle of claim 13 wherein the agrochemical is a herbicide, fungicide, bactericide, acaricide, insecticide, gametocide, nematocide, algicide, rodenticides, molluscides, insect baits, repellents, pheromones, insect growth regulators, fertilizers, micronutrients, soil conditioners, growth regulators or a mixture thereof.

15. The vehicle of claim 13 wherein the biopesticide is a fungus, virus, bacterium, toxin or a mixture thereof.

16. The vehicle of claim 12 wherein a second biocarrier comprising a plurality of discrete particles obtained from a plant material that is not soybeans is added to the biocarrier obtained from soybeans in an amount up to about 50 percent by weight based on the combined weight of the particles.

17. The vehicle of claim 16 wherein the plant material is obtained from wheat, corn or oats.

18. A process for preparing a fungal biopesticide biocarrier comprising the steps of:
 a) providing a biocarrier comprising a plurality of discrete particles obtained as a residual cell mass remaining after lipids and soluble proteins and sugars have been removed from crushed or ground oil seeds;
 b) mixing a fungal biopesticide with said particles in an amount up to 60% by weight of said mixture; and,
 c) processing the resulting mixture into powder, flakes, granules, pellets, tablets or briquettes.

19. The process of claim 18 wherein the oil seeds are crushed or ground soybeans and the residual cell mass includes cell walls, membranes and microfilaments.

20. The process of claim 19 wherein the fungal biopesticide is Lagenidium.

21. A delivery vehicle for delivering a fungal biopesticide comprising a plurality of discrete particles obtained as a residual cell mass remaining after lipids and soluble proteins and sugars been removed from crushed or ground oil seeds, said residual cell mass loaded with up to 60% by weight of a fungal biopesticide.

22. The delivery vehicle of claim 21 wherein the oil seeds are crushed or ground soybeans and said residual cell mass includes cell walls, membranes and microfilaments.

23. The delivery vehicle of claim 22 wherein the fungal biopesticide is Lagenidium.

\* \* \* \* \*